United States Patent [19]

Ryder et al.

[11] 4,414,975
[45] Nov. 15, 1983

[54] BLOOD LANCET

[75] Inventors: Francis E. Ryder; Michael D. Thomas, both of Arab, Ala.

[73] Assignee: Ryder International Corp., Arab, Ala.

[21] Appl. No.: 264,189

[22] Filed: May 15, 1981

[51] Int. Cl.³ .......................................... A61B 17/32
[52] U.S. Cl. ................................. 128/314; 128/329 R
[58] Field of Search ................. 128/314, 315, 329 R, 128/330; 30/367, 155, 159, 755; 604/22

[56] References Cited

U.S. PATENT DOCUMENTS

| 245,040 | 7/1977 | Thomas. | |
|---|---|---|---|
| 3,659,608 | 5/1972 | Perry | 128/314 |
| 3,760,809 | 9/1973 | Campbell | 128/314 |
| 4,203,446 | 5/1980 | Hofert et al. | 128/329 R |
| 4,230,118 | 10/1980 | Holman et al. | 128/314 |

*Primary Examiner*—Michael H. Thaler
*Attorney, Agent, or Firm*—Trexler, Bushnell & Wolters, Ltd.

[57] ABSTRACT

A disposable lancet for use in obtaining blood samples comprises a plastic housing and a resilient blade in a retracted position within the housing, the blade being bent in an arcuate form to provide a source of spring energy biasing the piercing edge of the blade toward an opening in the housing. A releasable trigger means retains the blade in its retracted position in the housing but is readily operable to release the blade to cause the part of the blade with the piercing edge to be driven through the opening a predetermined distance.

3 Claims, 10 Drawing Figures

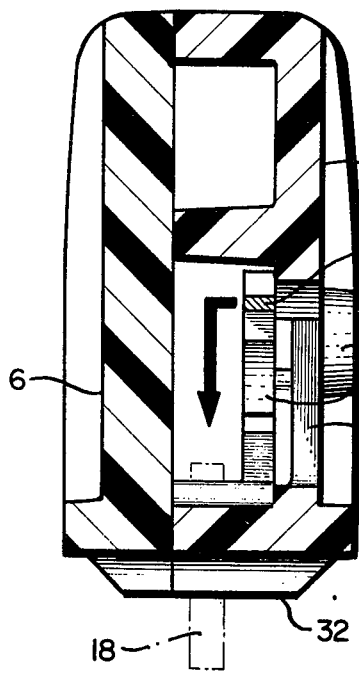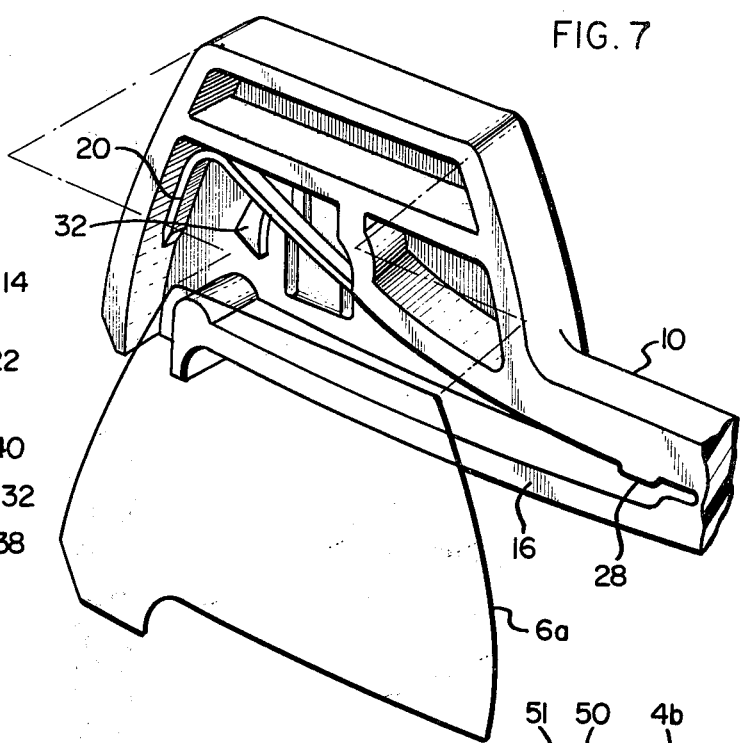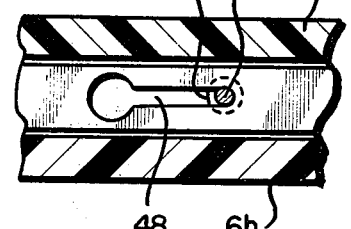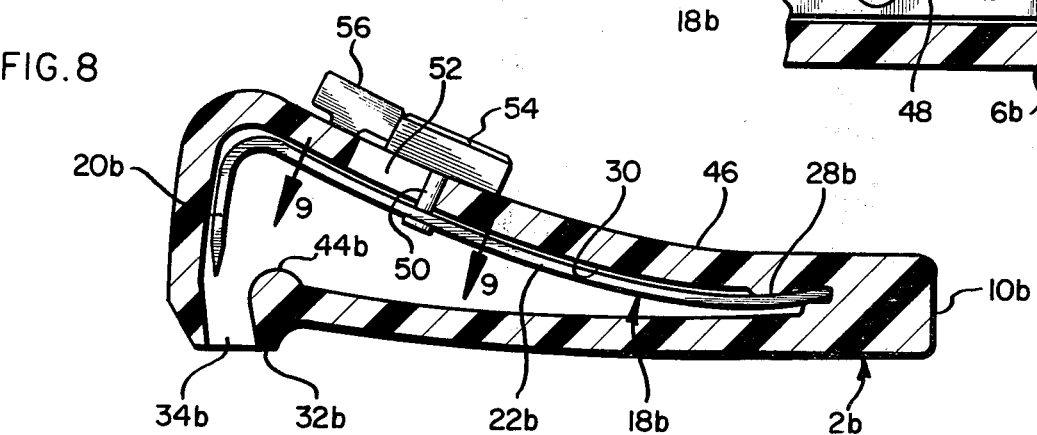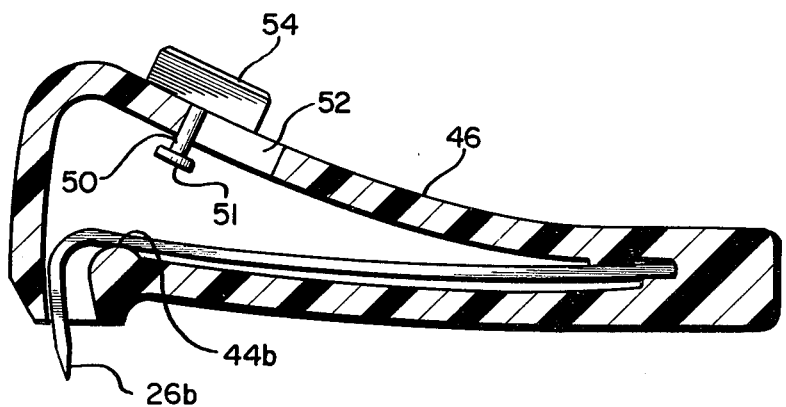

BLOOD LANCET

BACKGROUND OF THE INVENTION

This invention relates to new and useful improvements in blood lancets of the disposable or throw-away type.

Conventional blood lancets are typically formed with a blade having converging sides that terminate in a sharp point. The blade is connected to a handle of one sort or another so that the lancet may be grasped by the person operating the same. These lancets are often of the reuseable type, which requires resterilization after each use. However, the preferred medical practice militates against repeated sterilization of the blood lancets just as the same standard of medical practice avoids resterilization of hypodermic needles. The primary reason for using one-time or throw-away lancets is, therefore, the same as in the case of hypodermic needles, namely the avoidance of the risk of cross infection resulting from improper sterilization. Moreover, just as hypodermic needles tend to become dull or barbed with repeated handling so is it with lancets which, in analogous way, may have their blades dulled or distorted from repeated handling or use.

Another problem with blood lancets of the conventional type lies in the fact that they tend to look ominous to the patient who is sometimes apprehensive about being punctured with any kind of surgical instrument. Thus, the exposed blade of the lancet may tend to induce unnecessarily an uncomfortable or disturbed feeling in the patient.

While blood samples may be drawn in connection with a variety of tests, one well-known test commonly performed is known as the bleeding time test. This test evaluates hemostatic integrity, particularly platelet function, by measuring the time required for primary arrestive bleeding. This test is reliable only when the vascular wound is produced in a standardized manner. Consequently, the bleeding time procedure has become standardized with lancets that permit a precise length and depth of incision. Moreover, the precise incision makes the test more acceptable to the patient and more convenient for the clincian who is trying to determine the adequacy of primary hemostasis.

OBJECTS AND SUMMARY OF THE INVENTION

A primary object of this invention is to provide a blood lancet which is relatively inexpensive to construct and is of the disposable type.

A further object of this invention is to provide a blood lancet of the type stated in which the blade is concealed before use, and the incision is made almost instantaneously and as painlessly as is reasonably possible.

Yet another object of this invention is to provide a blood lancet of the type stated which is easily sterilized by gas sterilization processes after the lancet has been manufactured.

An additional object of this invention is to provide a lancet of the type stated in which the incision is of reasonably precise length and depth so as to make it easy for the physician to obtain reliable information on hemostasis, and especially platelet function.

In accordance with the foregoing objects the lancet comprising a housing including a wall portion with an opening into the housing, said wall portion having means surrounding the opening for placement against the skin of a patient, a resilient blade within said housing, said blade having first and second portions forming an angle, said first portion having a free end constituting an edge for penetration of a patient's skin, said blade having a retracted position in which said first portion is within said housing with said edge presented toward said opening and said second portion is bent in an arcuate form within its elastic limits to provide a source of spring energy biasing said edge toward said opening, and releasable triggering means for retaining said blade in its retracted position but operable to release said blade to cause the spring energy to drive said first portion and said edge through said opening.

The lancet is further constructed with said second portion having a free end at which said blade is secured in said housing to form a region of anchorage of said blade such that as said blade is released, it moves substantially as a cantilever.

Within the housing is fixed abutment or stop engageable by said second portion after the blade has been released such that the outward projection of said first portion from said means surrounding the opening is predetermined, whereby to provide an incision of predetermined depth in the patient's skin.

BRIEF DESCRIPTION OF THE FIGURES

FIG. 6 is a sectional view taken approximately along line 6—6 of FIG. 3;

FIG. 7 is an exploded perspective view of a modified form of lancet;

FIG. 8 is a longitudinal sectional view of yet another form of lancet constructed in accordance with the present invention and showing the blade retracted;

FIG. 9 is a fragmentary sectional view taken along line 9—9 of FIG. 8; and

FIG. 10 is a sectional view similar to FIG. 8 and showing the blade after it has been released.

DETAILED DESCRIPTION

Figure 1:
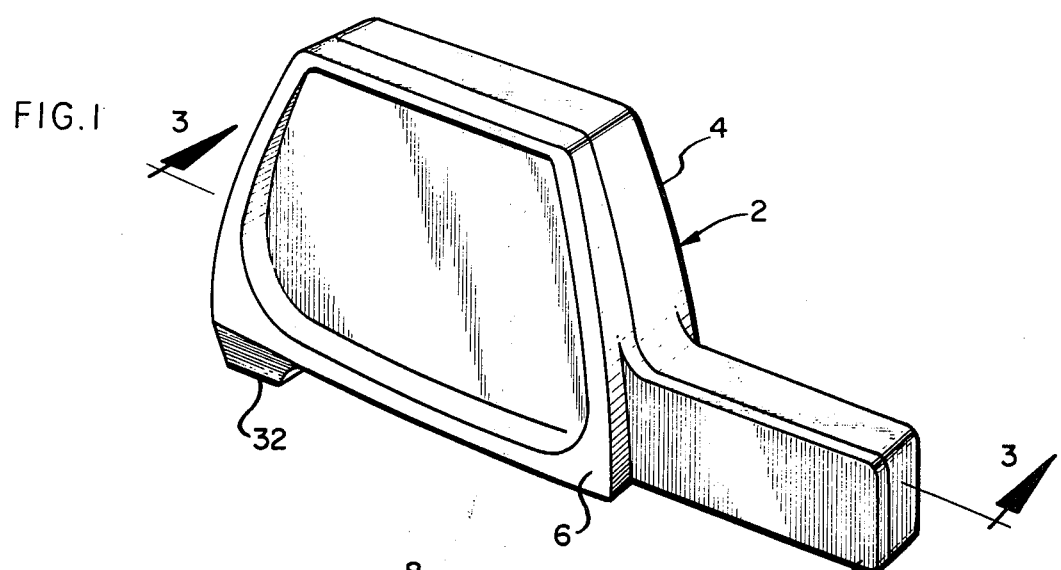
FIG. 1 is a perspective view of a lancet constructed in accordance with and embodying the present invention.
Figure 2:
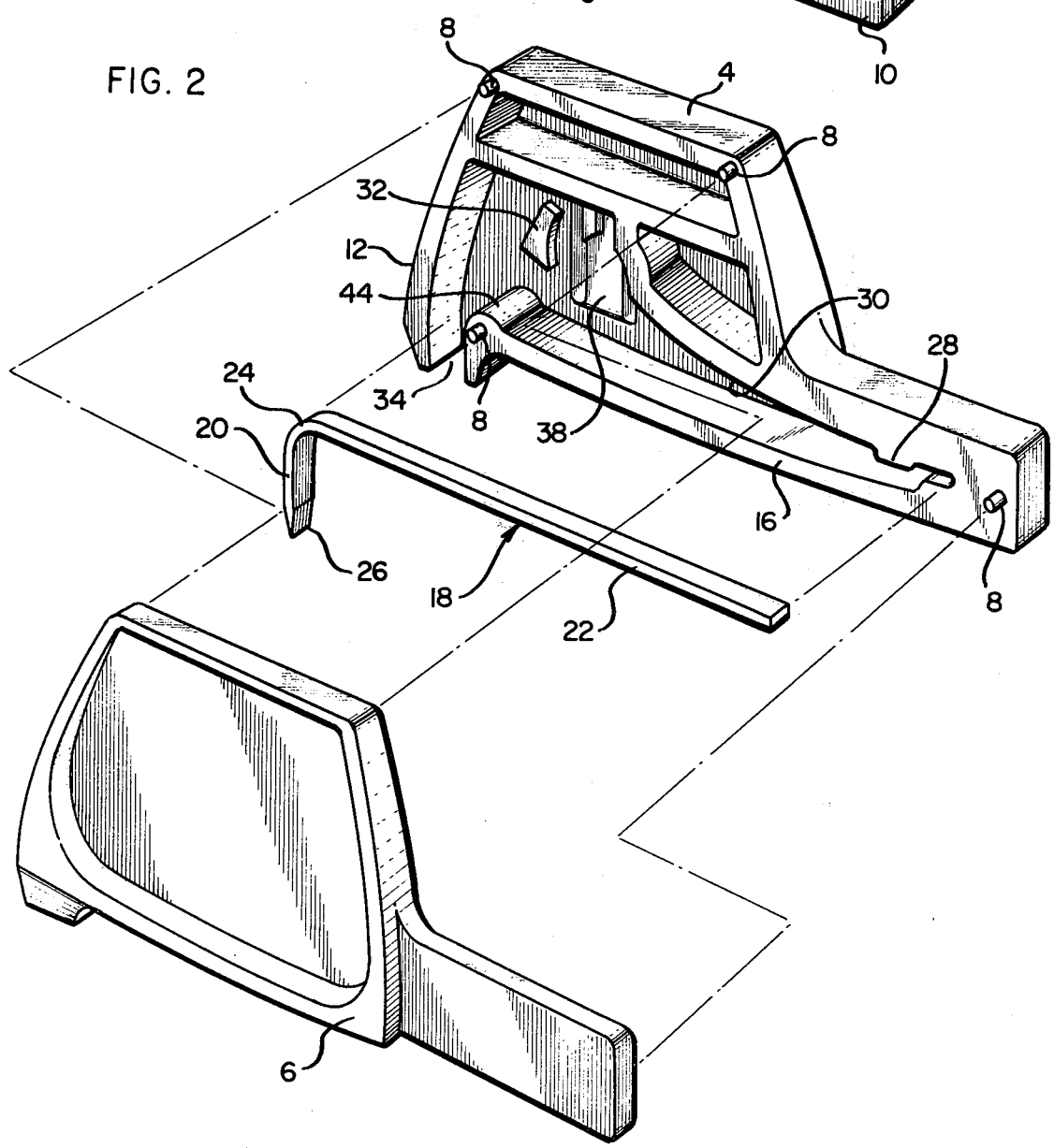
FIG. 2 is a fragmentary exploded perspective view of the lancet.

Referring now in more detail to the drawing there is shown a lancet comprising a housing 2 of a suitable plastic such as acetal resin sold under the trademark "Delrin". The housing 2 is made up of receptacle portion 4 that is open at one side and a closure portion 6 disposed over the open side of the receptacle portion 4. Receptacle portion 4 includes a plurality of pins 8 which fit into recesses (not shown) in the portion 6 whereby to facilitate assembly of the lancet. The two portions 4, 6 may be adhesively or otherwise secured together. When assembled, the housing 2 will include a generally rectilinear rear portion constituting a handle 10. The housing further includes a narrow front wall 12, a side wall 14 and bottom wall 16.

Within the housing 2 is a resilient metal blade 18 comprising a first portion 20 and a second portion 22 joined thereto by a curved short bight 24. In the unstressed condition the portions 20, 22 are substantially at right angles to each other. The free end of the first portion 20 has tapering sides that provide a sharp cutting edge 26.

Figure 3:
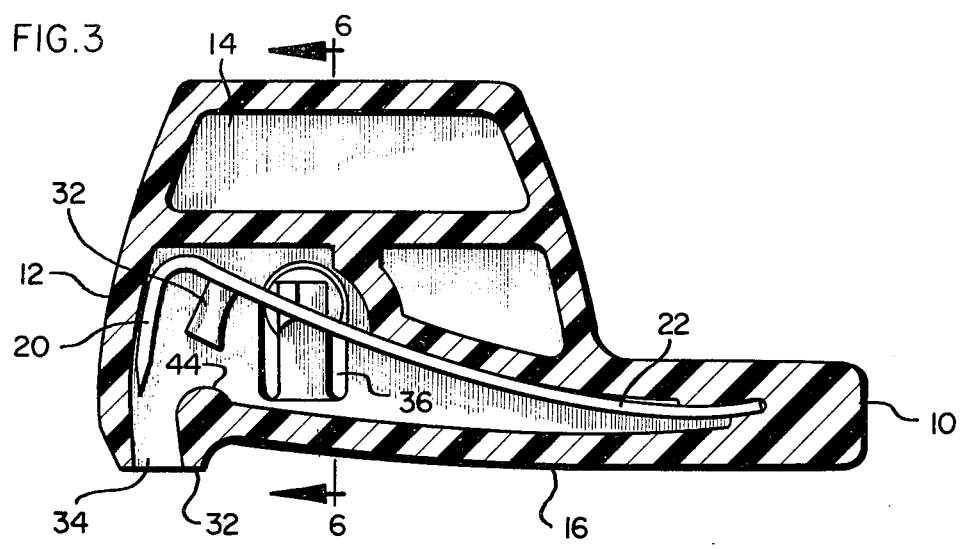
FIG. 3 is a sectional view taken along line 3—3 of FIG. 1 and showing a blade in its retracted position preparatory for use of the lancet.

When the blade 18 is assembled within the housing, the free end of the second portion 22 of the blade lies within the handle 8 and is lodged between the bottom wall 16 and a small boss 28 that projects from an arcuate forwardly extending surface 30. In assembly with the housing, the blade 18 is bent into an arcuate form within its elastic limits so that when the blade is in its retracted position as shown in FIG. 3, blade portion 22 adjacent to the bight 24 will seat upon an inwardly projecting shoulder 32 which is integral with the side wall 14. In this retracted position the second portion 22 may conform approximately to the arcuate surface 30 while leaving the blade portion 20 close to the front wall 12. Furthermore, the blade portion 20 with its cutting edge 26 is spaced from an opening 34 in the bottom wall 16. The lancet is shipped and stored with the blade retracted and in a sterilized condition.

Figure 4:
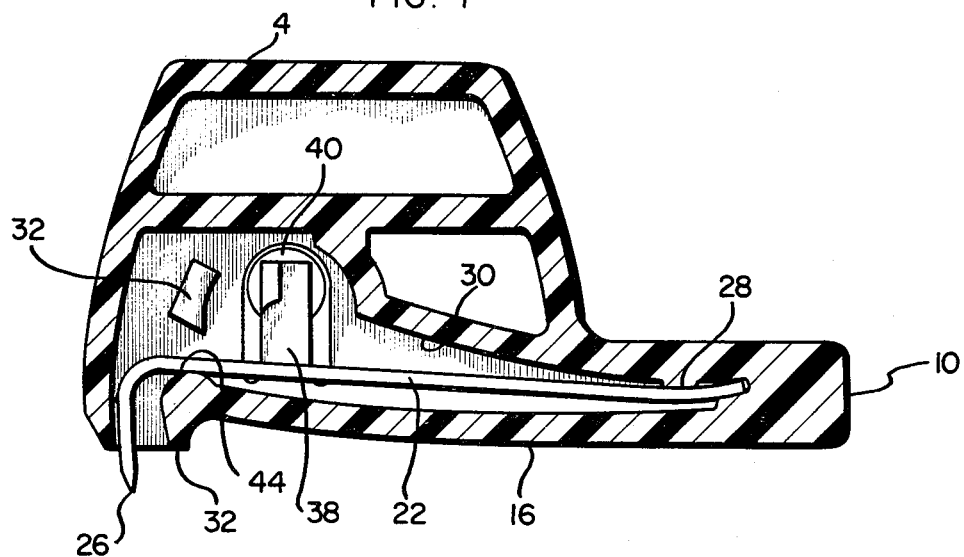
FIG. 4 is a sectional view similar to FIG. 3 but showing the lancet after the blade has been triggered or released.
Figure 5:
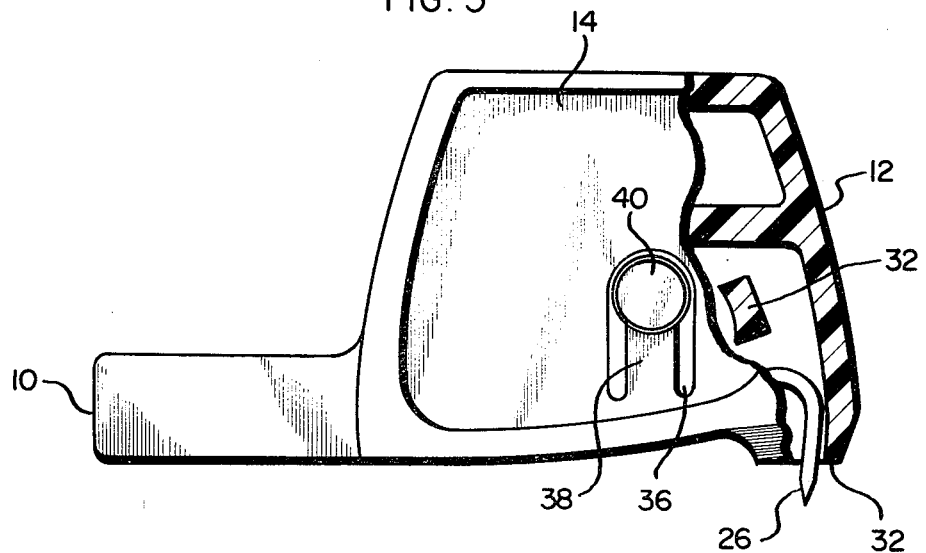
FIG. 5 is a side-elevational view, opposite to that seen in FIG. 1, partially broken and in section, and showing the lancet after the blade has been triggered.

A triggering means is utilized to release the blade from its retracted position. For this purpose the side wall 14 has an opening 36 at which there is molded a resilient tab 38, the base of which joins the side wall 14. This tab 38 is adjacent to the blade portion 22 and includes a button 40. When the button 40 is pressed inwardly the tab 38 will push the blade off of the shoulder 32 to cause the spring energy of the blade to drive the blade portion 20 and the cutting edge 26 through the opening 34, as shown in FIG. 4.

From the foregoing it will be seen that operation of the lancet is relatively simple. The user positions the lancet housing such that the rim 42 surrounding the opening 34 is placed against the skin of the patient. The button 40 is then pressed inwardly to release the lancet blade 18, which moves as a cantilever until it engages a stop 44 on the bottom wall 16. The stop 44 limits the penetration of the lancet into the patient's skin and insures a standardized incision in the patient.

A modified form of lancet is shown in FIG. 7 which differs from that previously described. More specifically, this modified form of the lancet dispenses with the molded closure portion 6. To close the open side of the receptacle portion 4, a section of sheet material 6A is provided. The sheet material 6A may be transparent or opaque, and includes an adhesive surface which permits it to be affixed in overlying relation to the open side of the receptacle portion 4. In the disclosed form the configuration of the portion 6a is such that it covers only a portion of the side opening of the housing portion 4. Thus, the handle portion of the lancet is open at one side to facilitate circulation of gas through the cavity of the housing that contains the blade 18. The unit of FIG. 7 thus readily lends itself to gas sterilization.

A further modified form of lancet is shown in FIGS. 8-10 wherein parts designated with the suffix "b" identify correspondingly numbered parts previously described in FIGS. 1-6 but without "b". Housing sections 4b, 6b are secured together to form a handle 10b. The top wall 46 of the housing provides the arcuate surface 30b against which the retracted blade portion 22b approximately lies. The blade portion 22b is formed with a longitudinal keyhole slot 48 through which a pin 50 projects, the pin 50 also projecting through a slot 52 in the top wall of the housing 2a. On the end of the pin 50 is a head 51 that is larger than the narrower part of the slot 48 but which is smaller than the wider end of the slot 48. On the other end of the pin 50 is a triggering button 54 which is normally held against movement by a safety tab 56 that is formed on the housing 2b. The safety tab 56 thus engages the button 54 so that the pin 50 is maintained in the narrower part of the keyhold slot 48 when the lancet blade is in its retracted position, as shown in FIGS. 8 and 9. However, when the safety tab 56 is torn off the button 54 may be pushed forwardly to move the pin 50 into the larger portion of the keyhole slot 48 whereupon the pin 50 no longer retains the blade and the spring energy of the blade 18 causes it to be released and to move into the position shown in FIG. 10 to make the incision in the patient.

The invention is claimed as follows:

1. A surgical lancet for use in obtaining a blood sample, or the like, said lancet comprising: a housing including a longitudinal side wall having a shoulder formed thereon, which shoulder extends transversely of the interior surface of said side wall; a resiliently biased blade member mounted within said housing, said blade member comprising a resilient strip of metal material including an elongate first portion having one end fixed with respect to the housing, and a relatively short, transverse second portion joined to said first portion at the other end thereof, said second portion including an edge for penetrating a patient's skin, said blade member being capable of being flexed to a first retracted position wherein the edge of said blade is disposed within the housing, with said first portion of the blade member engaged upon said shoulder extending transversely of the interior surface of the housing side wall and said blade member being moveable off said shoulder such that the resiliency of said blade member will cause it to move to a second extended position wherein the edge projects from an opening in said housing; and triggering means selectively operable to move said blade member transversely of the housing side wall and off said shoulder whereby said blade is then free to move from said first retracted position to said second extended position, said triggering means including a resilient tab formed integral with said housing side wall structure adjacent said shoulder, said tab, in its normal unstressed condition not extending inwardly of the interior surface of the housing side wall a sufficient distance to prevent engagement of the blade member on said shoulder, said tab being moveable transversely of said side wall such that said tab may be pressed inwardly to engage against said blade member and to move the blade member transversely of the side wall to disengage said blade member from said shoulder thereby permitting said blade to move from the retracted position to the extended position wherein the edge thereof projects from said housing.

2. A surgical lancet according to claim 1 wherein said housing includes a longitudinal side wall structure and is open along a longitudinal side thereof opposite said side wall structure to permit disposition and mounting of said blade within said housing, and a section of sheet material overlies open side to close said housing.

3. A surgical lancet according to claim 2 wherein said housing is of a two piece construction being divided longitudinally into two sections, with said triggering means and said blade means being associated with one of said sections.

* * * * *